(12) United States Patent
Mannheimer

(10) Patent No.: US 7,548,771 B2
(45) Date of Patent: Jun. 16, 2009

(54) PULSE OXIMETRY SENSOR AND TECHNIQUE FOR USING THE SAME ON A DISTAL REGION OF A PATIENT'S DIGIT

(75) Inventor: Paul D. Mannheimer, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 487 days.

(21) Appl. No.: 11/096,009

(22) Filed: Mar. 31, 2005

(65) Prior Publication Data

US 2006/0224058 A1 Oct. 5, 2006

(51) Int. Cl.
*A61B 5/1455* (2006.01)

(52) U.S. Cl. ...................................... 600/323; 600/344

(58) Field of Classification Search ................. 600/322, 600/323, 344
See application file for complete search history.

(56) References Cited

U.S. PATENT DOCUMENTS

| | | | | |
|---|---|---|---|---|
| 4,685,464 A | * | 8/1987 | Goldberger et al. | 600/344 |
| 4,830,014 A | | 5/1989 | Goodman et al. | |
| 5,246,003 A | * | 9/1993 | DeLonzor | 600/344 |
| 5,469,845 A | * | 11/1995 | DeLonzor et al. | 600/372 |
| 5,490,523 A | | 2/1996 | Isaacson et al. | |
| 5,678,544 A | * | 10/1997 | DeLonzor et al. | 600/344 |
| 5,776,059 A | | 7/1998 | Kaestle et al. | |
| 5,810,724 A | * | 9/1998 | Gronvall | 600/323 |
| 5,830,136 A | * | 11/1998 | Delonzor et al. | 600/323 |
| 5,924,982 A | * | 7/1999 | Chin | 600/310 |
| 6,018,673 A | * | 1/2000 | Chin et al. | 600/322 |
| 6,115,621 A | * | 9/2000 | Chin | 600/323 |
| 6,374,129 B1 | * | 4/2002 | Chin et al. | 600/322 |
| 6,697,656 B1 | * | 2/2004 | Al-Ali | 600/323 |
| 6,845,256 B2 | * | 1/2005 | Chin et al. | 600/323 |
| 7,260,425 B2 | * | 8/2007 | Chin et al. | 600/323 |
| 2002/0103423 A1 | | 8/2002 | Chin et al. | |
| 2002/0115919 A1 | * | 8/2002 | Al-Ali | 600/323 |
| 2005/0070773 A1 | * | 3/2005 | Chin et al. | 600/322 |
| 2007/0073124 A1 | * | 3/2007 | Li et al. | 600/323 |

FOREIGN PATENT DOCUMENTS

| | | |
|---|---|---|
| EP | 0 781 527 A | 7/1997 |
| EP | 1 222 894 A | 7/2002 |

* cited by examiner

*Primary Examiner*—Eric F Winakur
*Assistant Examiner*—Etsub D Berhanu
(74) *Attorney, Agent, or Firm*—Fletcher Yoder

(57) ABSTRACT

A sensor may be placed on a distal portion of a patient's finger or toe to obtain pulse oximetry measurements. The distal portion of a digit contains few if any large vascular structures that could adversely affect pulse oximetry measurements, but the distal portion does contain microvasculature that carries arterial blood that facilitates pulse oximetry measurements. The sensor may include an emitter and a detector that are spaced apart by an appropriate distance so that they may be located on the distal portion of a patient's digit during pulse oximetry measurements.

32 Claims, 7 Drawing Sheets

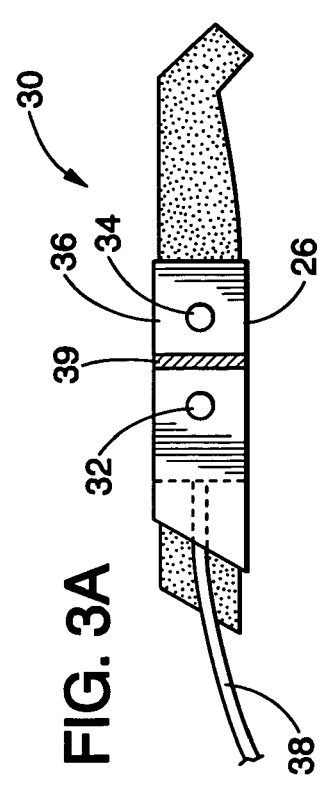
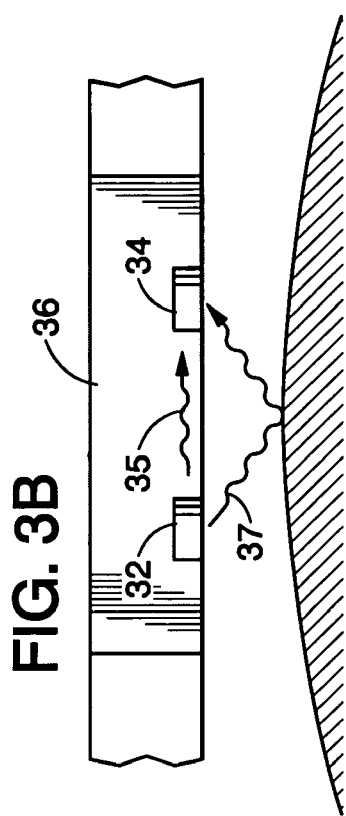
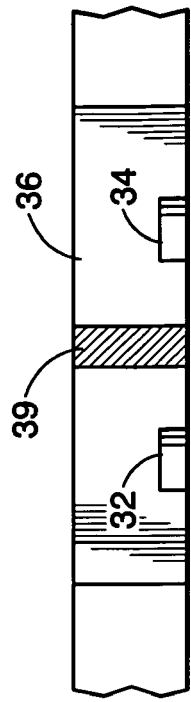
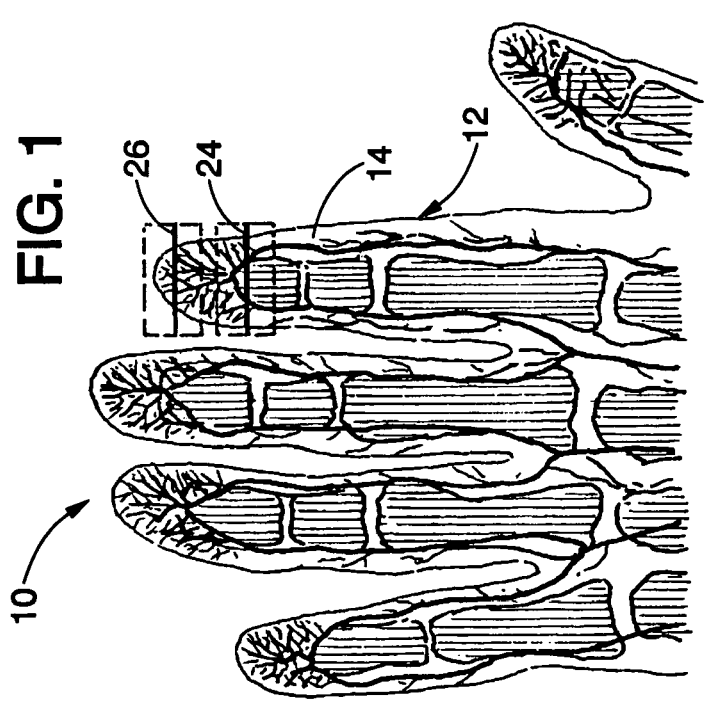
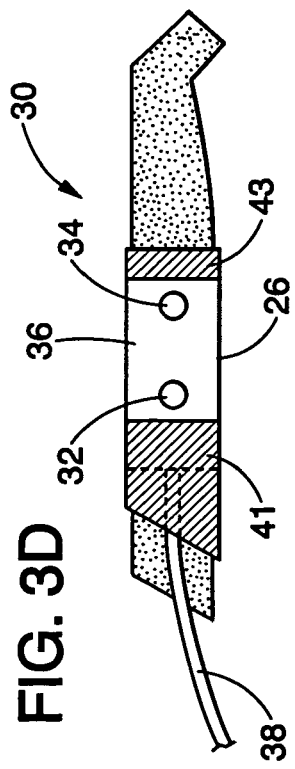

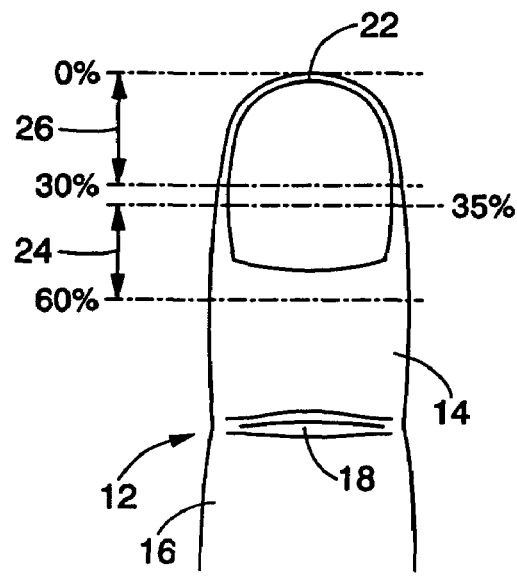
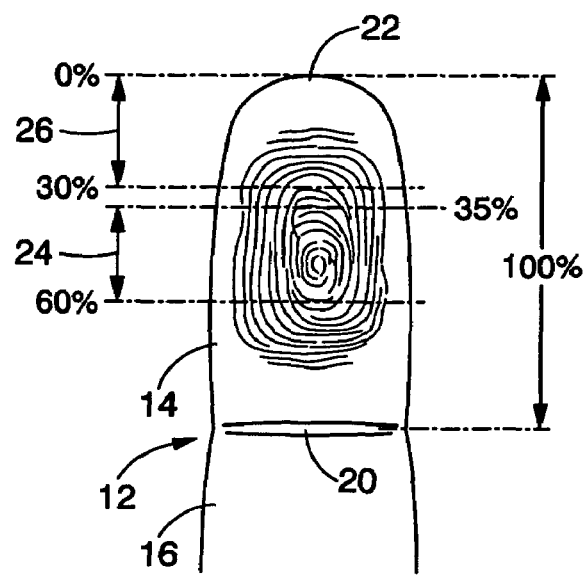
FIG. 2A  FIG. 2B
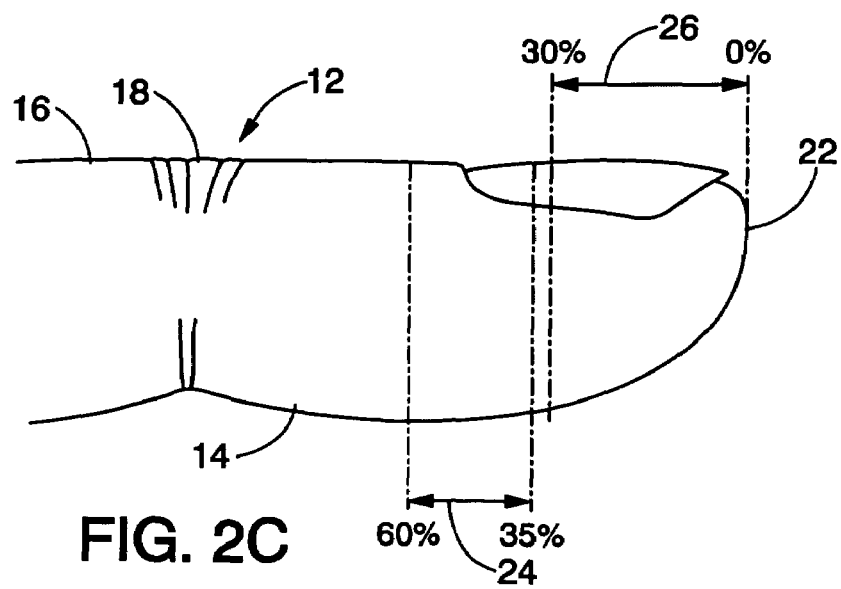
FIG. 2C

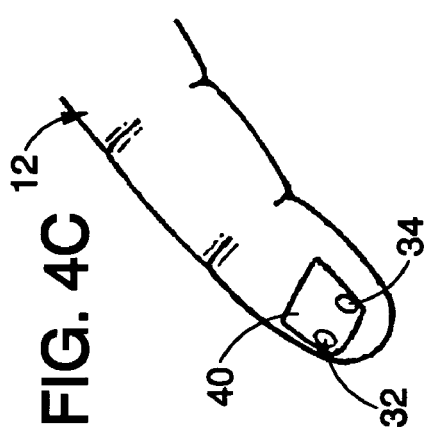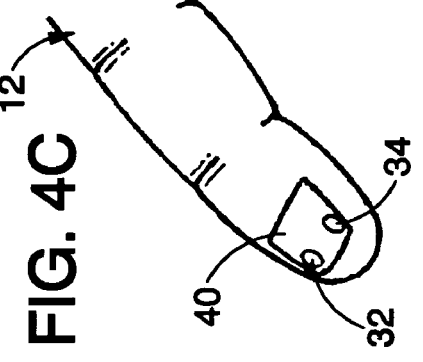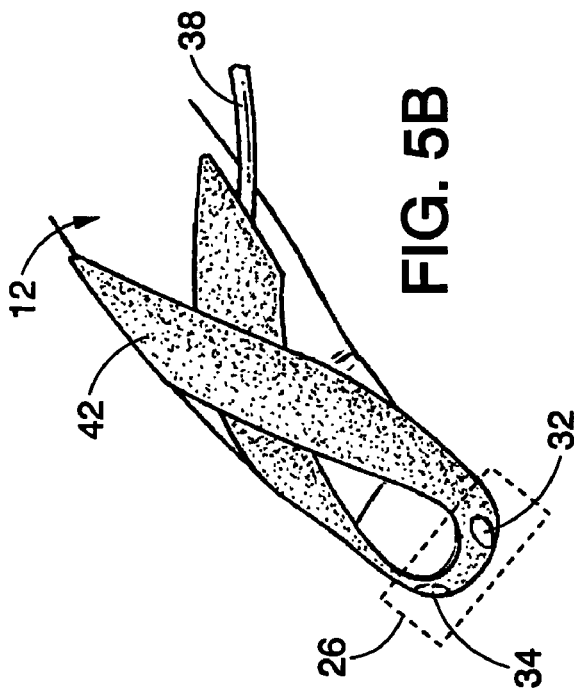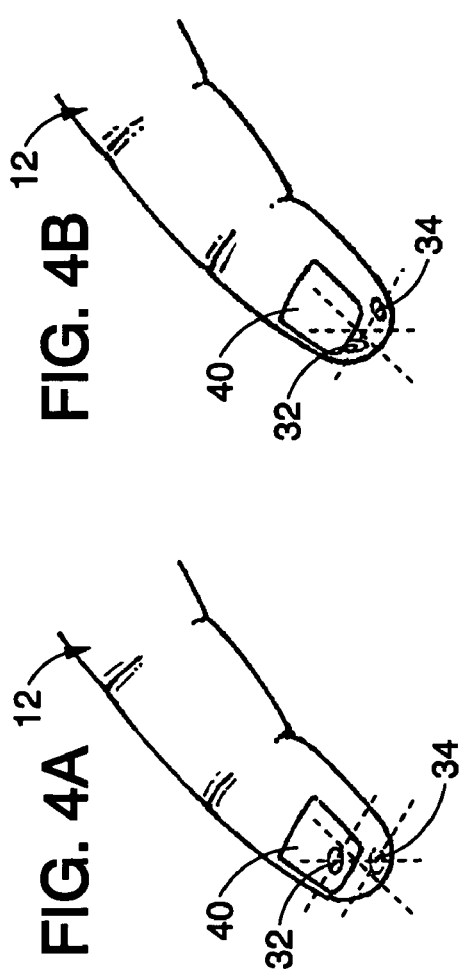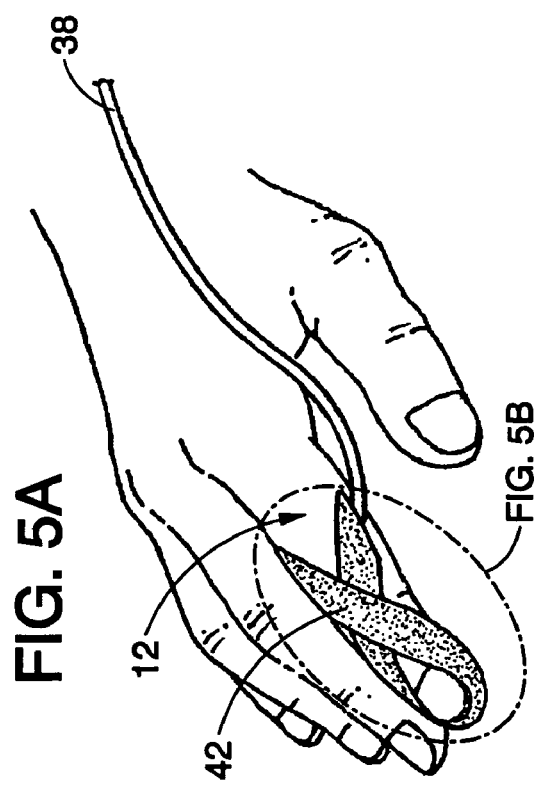

PULSE OXIMETRY SENSOR AND TECHNIQUE FOR USING THE SAME ON A DISTAL REGION OF A PATIENT'S DIGIT

BACKGROUND OF THE INVENTION

1. Field of the Invention

The present invention relates generally to pulse oximetry and, more particularly, to sensors used for pulse oximetry.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically senses the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms. Changes in the amount of arterial blood in the tissue during a blood pressure pulse may change the amount and character of the light detected by the sensor's photodetector.

The quality of the pulse oximetry measurement depends in part on the concentration of arterial blood relative to other tissue structures in the portion of the tissue illuminated by the sensor and in part on the magnitude of the pulsatile changes in the amount of blood in the tissue. Pulse oximetry techniques typically utilize a tissue site that is well perfused with blood, such as a patient's finger, toe, or earlobe, on which to place the sensor. Although these sites are usually well perfused, blood flow to the sensor site may be restricted due to the effects of ambient temperature, systemically acting vasoconstricting drugs in the patient's blood stream, or low blood pressure. The accuracy and reliability of physiological measurements can be affected by the amount of blood perfusion, as well as by the distribution of blood flow within a tissue site. Furthermore, physiological differences from patient to patient, or even from digit to digit, may cause unintended variations in the measurements provided.

BRIEF DESCRIPTION OF THE DRAWINGS

Advantages of the invention may become apparent upon reading the following detailed description and upon reference to the drawings in which:

FIG. 1 illustrates an exemplary patient's fingers illustrating bone and blood vessel placement;

FIGS. 2A, 2B, and 2C illustrate different views of an exemplary patient's finger illustrating an exemplary cuticle region and an exemplary distal region;

FIGS. 3A and 3D illustrate alternative embodiments of an exemplary pulse oximetry sensor adapted for placement on a distal region of a patient's digit;

FIG. 3B illustrates exemplary shunting characteristics of a pulse oximetry sensor;

FIG. 3C illustrates a cross-section of the pulse oximetry sensor of FIG. 3A with a shunt block;

FIGS. 4A, 4B and 4C illustrate alternative placements of the emitter and detector of an exemplary pulse oximetry sensor in accordance with the present invention.

FIG. 5A illustrates an exemplary bandage for securing the pulse oximetry sensor of FIG. 3 to a patient's hand;

FIG. 5B illustrates a detailed view of the highlighted area of FIG. 5A;

DETAILED DESCRIPTION OF SPECIFIC EMBODIMENTS

Figure 6A:
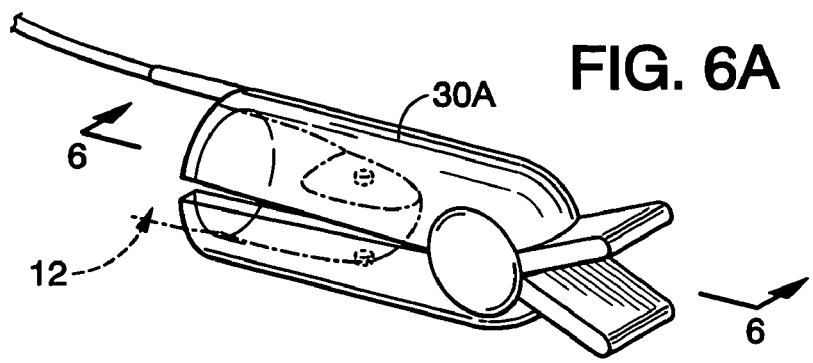
FIG. 6A illustrates a perspective view of an exemplary clip-style pulse oximetry sensor on a patient's finger.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed previously, pulse oximetry sensors are typically placed on a patient in a location that is normally perfused with arterial blood to facilitate proper light absorption. The most common sensor sites include a patient's fingertips, toes, or earlobes. Pulse oximetry sensors used on these sensor sites are typically "transmission type" sensors. Transmission type sensors include an emitter and detector that are typically placed on opposing sides of the sensor site. If the sensor site is a fingertip, for example, the cuff, clip, or bandage associated with the pulse oximetry sensor is positioned over the patient's fingertip such that the emitter and detector lie on either side of the patient's nail bed. In other words, the sensor is positioned so that the emitter is located on the patient's fingernail and the detector is located 180° opposite the emitter on the patient's finger pad. During operation, the emitter shines one or more wavelengths of light through the patient's fingertip, and the light received by the detector is processed to determine various physiological characteristics of the patient. For determining the oxygen saturation of the patient's arterial blood, two or more wavelengths are used, most commonly red and near infrared wavelengths.

Unfortunately, person-to-person and digit-to-digit variability, as well as sensor placement variability, can cause variability in the resulting pulse oximeter measurements. This variability stems, in part, from the unique inhomogenity of the vasculature within any specific sample of tissue and, in particular, the moving and pulsing structures, e.g., the arteries, within the tissue that non-linearly contribute to the optical density of the probed tissue bed. Further, the presence of larger subcutaneous vessels within the optically probed tissues may influence the relationship between the modulation ratio of the time-varying light transmission signals of the two or more wavelengths and the underlying arterial oxygen saturation measurement ($SaO_2$). Also, simply shifting the placement location of a sensor by as little as a few millimeters can result in changes in the measured blood oxygen saturation ($SpO_2$) of a few percent.

To address these concerns, it would be desirable to find a sensor site that is relatively void of larger semi-opaque vessels, but that includes microvasulature, such as arterioles and capillaries. Such a site would be well-perfused with arterial blood, yet devoid of larger vessels and/or translucent structures that might adversely affect the measurement capabilities of the sensor. The hand structure 10 shown in FIG. 1 indicates that the density of larger diameter arteries diminishes towards the distal end of the fingertips. Hence, a pulse oximetry technique designed to utilize the distal end of the fingertips, as opposed to a more proximal region of the fingertips, as a sensor site would benefit from tissue well-perfused with arterial blood, yet lacking larger vessels and/or translucent structures that might adversely affect the measurement capabilities of the sensor.

Looking also to FIGS. 2A, 2B, and 2C, a human finger, such as the patient's index finger 12, includes three bones, called phalanges. The bone that comprises the tip of the finger 12 is commonly referred to as the third row phalange or the distal phalange 14. On the exterior of the finger 12, the location of the joint between the distal phalange 14 and the second row phalange 16 can be identified by the knuckle 18 on the top of the finger 12 and by the transverse fold 20 of skin on the bottom of the finger 12.

The emitter and detector components of conventional pulse oximetry sensors are located close to the cuticle region of the fingernail, as indicated by the cuticle region 24 of the patient's index finger 12. If the overall length L of the distal phalange 14 (covered with skin and other tissue) is defined to extend from the tip 22 of the finger 12 to the transverse fold 20, then the cuticle region 24 extends from a transverse line spaced from the tip by about 35% of the length L to a transverse line spaced from the tip 22 by about 60% of the length L. In the cuticle region 24, several arteries can be seen that are much larger in diameter than the vasculature in the more distal region 26, which is defined herein to extend from the tip 22 to a transverse line spaced from the tip 22 by about 20% to about 30% of the length L. Hence, this conventional placement site in the cuticle region 24 is likely to cause measurement variations from patient-to-patient.

Indeed, it should be noted that each of the digits of the hand shown in the hand structure 10 have unique vessel locations. Thus, the placement of a pulse oximetry sensor over a similar cuticle region 24 of these digits may result in different signal modulations unrelated to the underlying $SaO_2$ level, since these larger vessels are sufficiently opaque and, thus, may non-linearly contribute to the optical density of the tissue. Furthermore, small variations in the precise location of the sensor optics in the cuticle region 24, or from digit-to-digit as illustrated in this hand structure 10, may result in different detected light levels due, in part, to the varying contribution of the more opaque larger vasculature. In turn, this may impact the detected red-to-infrared modulation ratio and, consequently, the measured $SpO_2$ value.

In sharp contrast, it should be noted that the distal region 26 of the index finger 12, i.e., the area extending from the tip 22 to a transverse line spaced from the tip 22 by between about 20% to about 30% of the length L (approximately 5 mm to 7 mm from the tip for an average adult finger), includes few, if any, larger diameter arteries that may adversely affect pulse oximetry measurements. Indeed, it appears that the light from a pulse oximeter sensor will scatter through the tissue in the distal region 24 to probe the smaller arterioles and capillaries more uniformly, since the light fully penetrates these vessels. It is believed that this manner in which the light probes the more uniform tissue results in a more linear relationship between the modulating, i.e., cardiac-induced time-varying, optical density of the tissue and the underlying arterial blood oxygen saturation. As a further result, it is believed that small variations in sensor placement in the distal region 26, as well as different digit-to-digit placements, will yield a more consistent relationship between the measured red-to-infrared modulation ratio and the underlying $SaO_2$ level than is observed when sensors are placed more proximally in the cuticle region 24.

To facilitate measurement in the distal region 26, a sensor having an emitter and detector that may be located in the distal region 26 of a patient's finger or toe is provided, and FIG. 3A illustrates an exemplary pulse oximetry sensor 30 of this type. The sensor 30 includes an emitter 32 and a detector 34 which may be of any suitable type. For example, the emitter 32 may be one or more light emitting diodes adapted to transmit one or more wavelengths of light in the red to infrared range, and the detector 34 may be a photodetector selected to receive light in the range emitted from the emitter 32. The emitter 32 and the detector 34 may be disposed on a substrate 36, which may be made of any suitable material, such as plastic, foam, woven material, or paper. Alternatively, the emitter 32 and the detector 34 may be located remotely and optically coupled to the sensor using optical fibers. The substrate 36 may include an adhesive thereon to facilitate coupling of the sensor 30 to the distal region 26 of a patient, although alternative coupling arrangements are discussed below. Finally, the sensor 30 is coupled to a cable 38 that is responsible for transmitting electrical and/or optical signals to and from the emitter 32 and detector 34 of the sensor 30. The cable 38 may be permanently coupled to the sensor 30, or it may be removably coupled to the sensor 30—the latter alternative being more useful and cost efficient in situations where the sensor 30 is disposable.

In one embodiment, the sensor 30 may be adapted to block light that may shunt directly between the emitter 32 and the detector 34, i.e., light that does not travel through the blood perfused tissue of the finger 12. An example of two possible shunting situations is illustrated in FIG. 3B. In one situation, a "type 1" shunt may occur when light travels from the emitter 32 to the detector 34 through the substrate 36, as illustrated by the wavy arrow 35. In another situation, a "type 2" shunt may occur when light travels from the emitter 32 to the detector 34 by reflecting off of the finger 12, as illustrated by the wavy arrow 37. While the type 2 shunt is typically addressed by ensuring that the sensor 30 is placed snuggly against the patient's finger 12, the type 1 shunt may be addressed by placing a shunt barrier 39 in or on the substrate 36 between the emitter 32 and the detector 34. A "type 3" shunt, which is not illustrated, could also occur if light passed through exsanguinated tissue.

In another embodiment, the sensor 30 may include regions that differ in the manner in which they reflect and/or absorb light from the emitter 32. As illustrated in FIG. 3D, it can be seen that the region of the substrate 36 that extends from the emitter 32 to the detector 34 may be a relatively light color, such as white, in order to enhance the reflectivity of the substrate 36 on the portion of the sensor 30 that is to be disposed on the distal region 26 of a patient's finger 12. Portions 41 and 43 of the substrate 36 that extend on either side of the emitter 32 and the detector 34 may be a darker, i.e., more absorptive, color, such as black. The darker portions 41 and 43 of the substrate 36 will tend to absorb the light from the emitter 32 from portions of a patient's finger 12 that may fall outside of the distal region 26 so that the light is not collected by the detector 34. Consequently, it is more likely that light detected by the detector 34 has passed through tissue in the distal region 26 of the patient's finger 12 as opposed to more proximal areas of the patient's finger 12.

It should be appreciated that the emitter 32 and detector 34 of the sensor 30 may be placed in various positions in the distal region 26 and may operate in various modes, e.g., transmission or reflection. Examples of placement positions of the emitter 32 and the detector 34 on a patient's finger 12 are illustrated in FIGS. 4A, 4B and 4C, although it should be appreciated that the emitter 32 and the detector 34 may be similarly placed on a patient's toe as well. In FIG. 4A, it can be seen that the emitter 32 is located on top of the finger 12 in the distal region 26, while the detector 34 is located underneath, i.e., on the finger pad, of the finger 12 in the distal region 26. The emitter 32 may lie slightly on the fingernail 40, slightly under the fingernail 40, or on a fleshy portion of the tip of the finger 12 that may protrude past the fingernail 40. In this example, the emitter 32 and detector 34 can be arranged in a transmission mode so that the light from the emitter 32 shines vertically through the finger 12 to the detector 34. For a sensor 30 designed for use on a normally-sized adult, the linear spacing between the center of the emitter 32 and the center of the detector 34 on the substrate 36 would be in the range of about 10 mm to about 20 mm to ensure that the emitter 32 and the detector 34 are properly positioned in the distal region 26 of the patient's finger when the sensor 30 is applied.

Alternate arrangements are illustrated in FIGS. 4B and 4C. In FIG. 4B, it can be seen that the emitter 32 and the detector 34 are both located underneath the finger 12, i.e., on the finger pad, in the distal region 26. Conversely, in FIG. 4C, it can be seen that the emitter 32 and the detector 34 are both located on the top of the finger 12 in the distal region 26. In the latter case, the emitter 32 and the detector 34 may both be placed slightly on the fingernail 40, slightly underneath the fingernail 40, or on the fleshy region of the tip of the finger 12 that may protrude past the fingernail 40. Because the emitter 32 and the detector 34 both lie on the same side of the finger 12 in the alternatives illustrated in FIGS. 4B and 4C, the emitter 32 and detector 34 may be considered to operate in reflectance mode instead of transmission mode. For a sensor 30 designed for use on a normally-sized adult, the linear spacing between the center of the emitter 32 and the center of the detector 34 on the substrate 36 would be in the range of about 5 mm to about 10 mm to ensure that the emitter 32 and the detector 34 are properly positioned in the distal region 26 of the patient's finger when the sensor 30 is applied.

In each of the embodiments discussed herein, it should be understood that the locations of the emitter and the detector may be swapped. For example, in FIG. 4A, the detector 34 may be located at the top of the finger 12 and the emitter 32 may be located underneath the finger 12. In either arrangement, the components are located in the distal region 26 and perform in substantially the same manner.

The sensor 30 may be applied to a patient's finger or toe in any suitable manner. One manner of application includes the use of an adhesive bandage 42, as illustrated in FIGS. 5A and 5B. In this example, the back of the substrate 36 is affixed to a portion of the adhesive bandage 42 so that the emitter 32 and detector 34 may be placed over the distal region 26 of the patient's finger 12. The adhesive bandage 42 may be wrapped over the entire finger, or it can be restricted to only a part of the finger. In this example, the adhesive bandage 42 is applied primarily to the top of the finger 12, where a portion of the bandage 42 extends along the cable 38. The bandage 42 is first adhered to the left side of the top of the patient's finger 12, extended to the right of the finger 12, around the distal region 26, and over to the right side of the finger 12 in overlapping relationship with itself. Although the illustrated example is believed to be particularly useful, any other suitable configuration may also be used. For example, the sensor 30 may be secured to the distal region 26 of a patient's finger 12 by a non-adhesive wrap, a reusable wrap, or a clip.

Figure 6B:
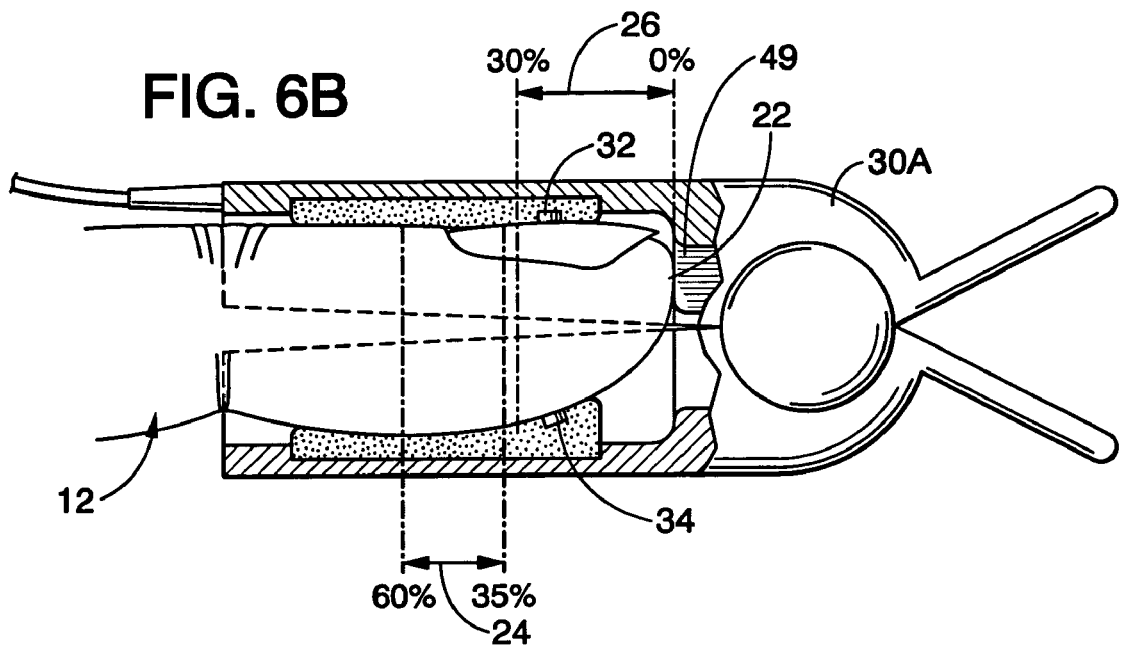
FIG. 6B illustrates a cross-sectional view of an exemplary clip-style pulse oximetry sensor having an emitter and detector located on a distal region of a patient's finger.
Figure 6C:
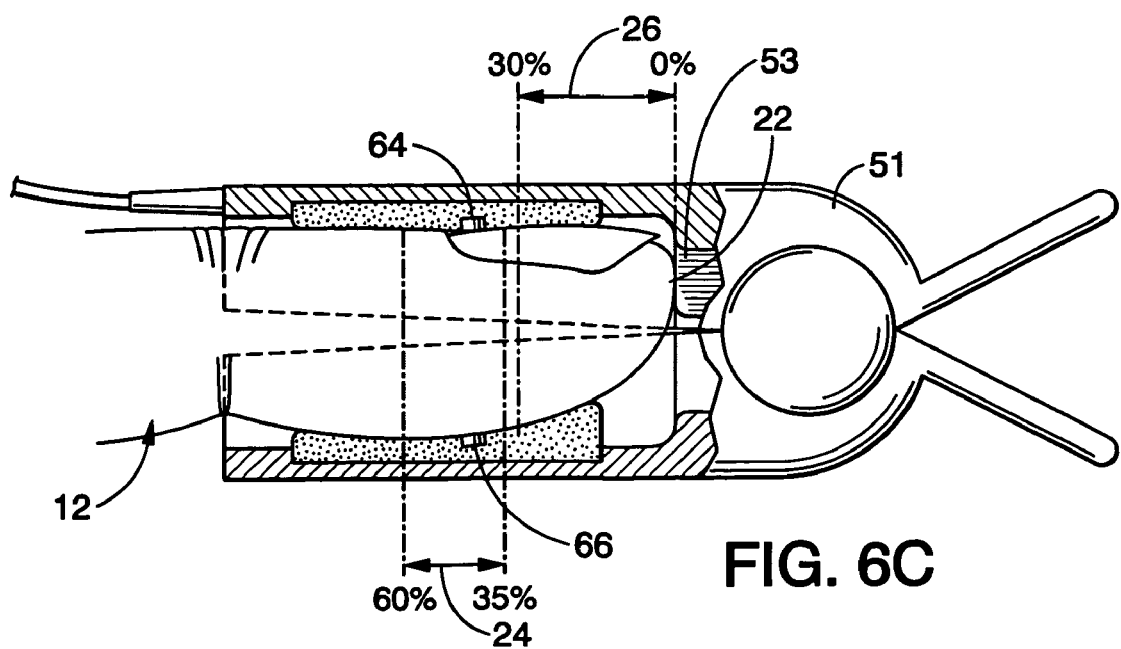
FIG. 6C illustrates a cross-sectional view of an exemplary clip-style pulse oximetry sensor having an emitter and detector located on a cuticle region of a patient's finger.

One example of a clip-style sensor 30A is illustrated in FIGS. 6A, 6B, and 6C. The sensor 30A is illustrated as having two halves or portions. In this embodiment, the sendor 30A is configured to operate in transmission mode, so the emitter resides in one half and the detector resides in the other half. In an alternate embodiment (not shown), the sensor 30A may be configured to operate in reflectance mode, in which case the emitter and the detector would reside in the same half or portion. In either case, the sensor 30A is spring loaded so that the sensor 30A is biased in a closed position about a patient's finger 12, as illustrated. As best seen in FIG. 6B, the sensor 30A includes a stop 49 upon which a patient's finger 12 is intended to rest when the patient's finger 12 is properly inserted into the clip-style sensor 30A. When the patient's finger 12 is properly inserted against the stop 49, the emitter 32 and the detector 34 lie in the distal region 26 of the patient's finger 12. In contrast to the sensor 30A illustrated in FIG. 6B, FIG. 6C illustrates a clip-style sensor 51 having a stop 53. As can be seen in FIG. 6C, when the patient's finger 12 is inserted to abut against the stop 53, the emitter 64 and the detector 66 are located in the cuticle region 24 of the patient's finger 12. Hence, it can be readily appreciated that the distance that the emitter and detector are spaced apart from the stop dictates whether the sensor is suitable for facilitating measurement in the distal region 26 or the cuticle region 24.

Figure 7:
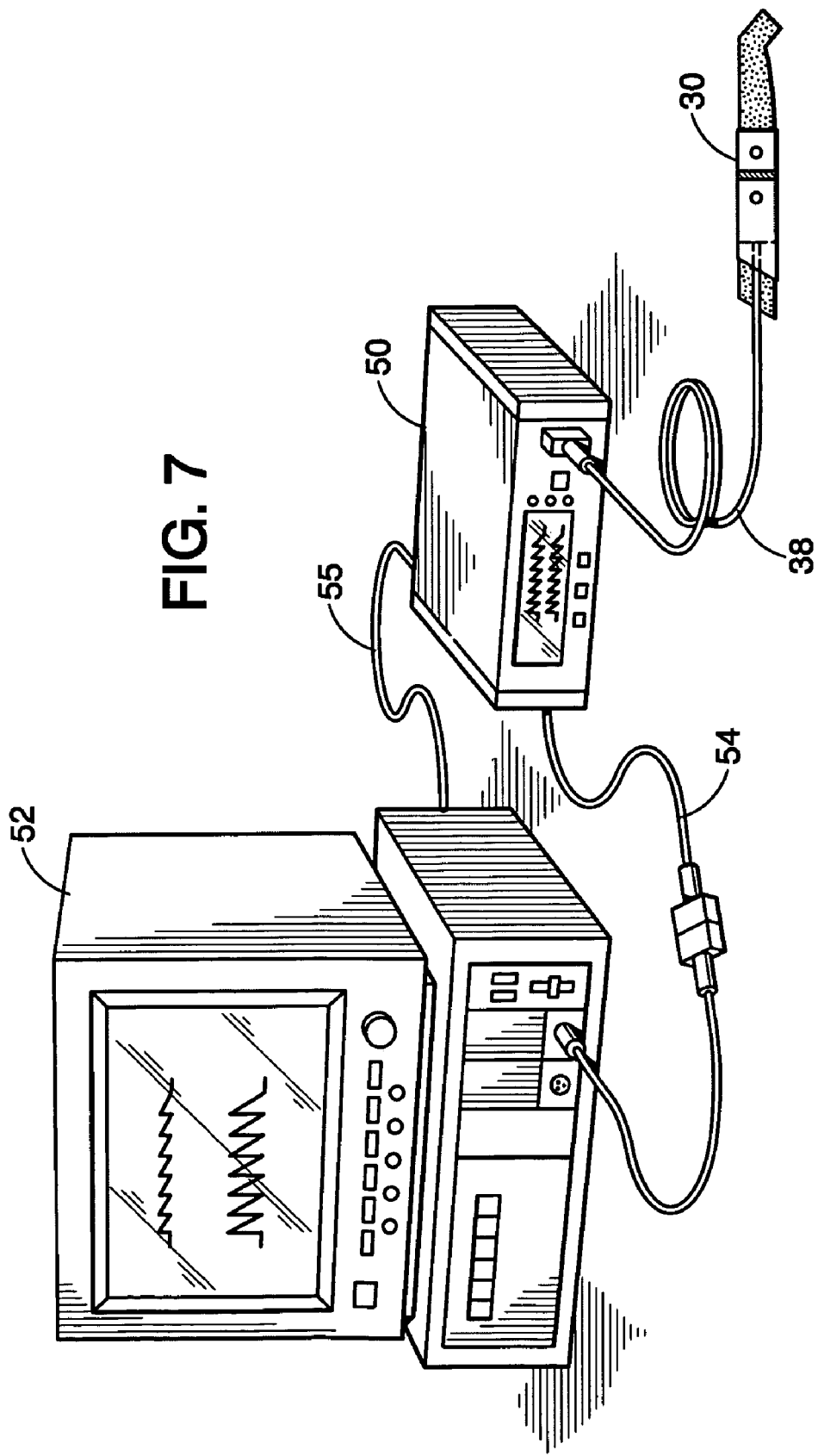
FIG. 7 illustrates a pulse oximetry system coupled to a multi-parameter patient monitor.

Regardless of type, the sensor 30 is typically adapted to be coupled directly to a pulse oximetry monitor 50, as illustrated in FIG. 7. However, it should be appreciated, that the cable 38 of the sensor 30 may be coupled to a transmission device (not shown) to facilitate wireless transmission between the sensor 30 and the monitor 50. The monitor 50 may be any suitable pulse oximeter, such as those available from Nellcor Puritan Bennett Inc. Furthermore, to upgrade conventional pulse oximetry provided by the monitor 50 to provide additional functions, the monitor 50 may be coupled to a multi-parameter patient monitor or other pulse oximetry monitor 52 via a cable 54 connected to a sensor input port or via a cable 55 connected to a digital communication port.

Figure 8A:
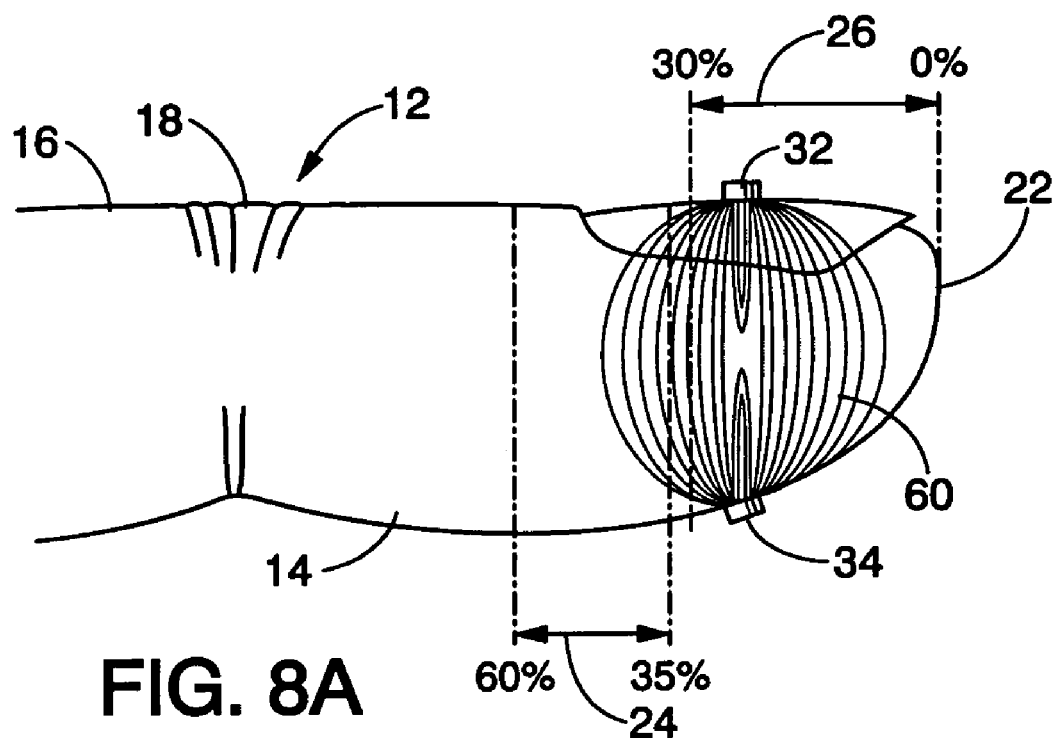
FIG. 8A illustrates an exemplary photon distribution through a patient's finger for a pulse oximetry sensor placed on a distal region of a patient's finger.

Once the sensor 30 is suitably applied to the distal region 26 of the patient's finger 12 and coupled to a suitable pulse oximetry monitor, the emitter 32 will transmit the selected wavelength(s) of light into the distal region 26 of the patient's finger 12 and the detector 34 will detect light from the distal region 26 of the patient's finger 12. As illustrated in FIG. 8A, the photon distribution 60 illustrates the amount of light emitted from the emitter 32 that passes through various portions of the patient's finger 12 and that is detected by the detector 34. In other words, the photon distribution 60 is a graphical representation of where the photons from the emitter 32 travel through the tissue for ultimate receipt by the detector 34. With the emitter 32 and detector 34 located in the distal region 26 of the patient's finger 12, it can be seen that the majority of the photons received by the detector 34 pass through the distal region 26, with a minority of the photons received by the detector 34 passing through the cuticle region 24. Indeed, it is estimated that at least approximately 50% to 80%, and possibly 90% or more, of the light received by the detector 34 has passed through the distal region 26 when the sensor 30 is located in the distal region 26 of the patient's finger 12.

Figure 8B:
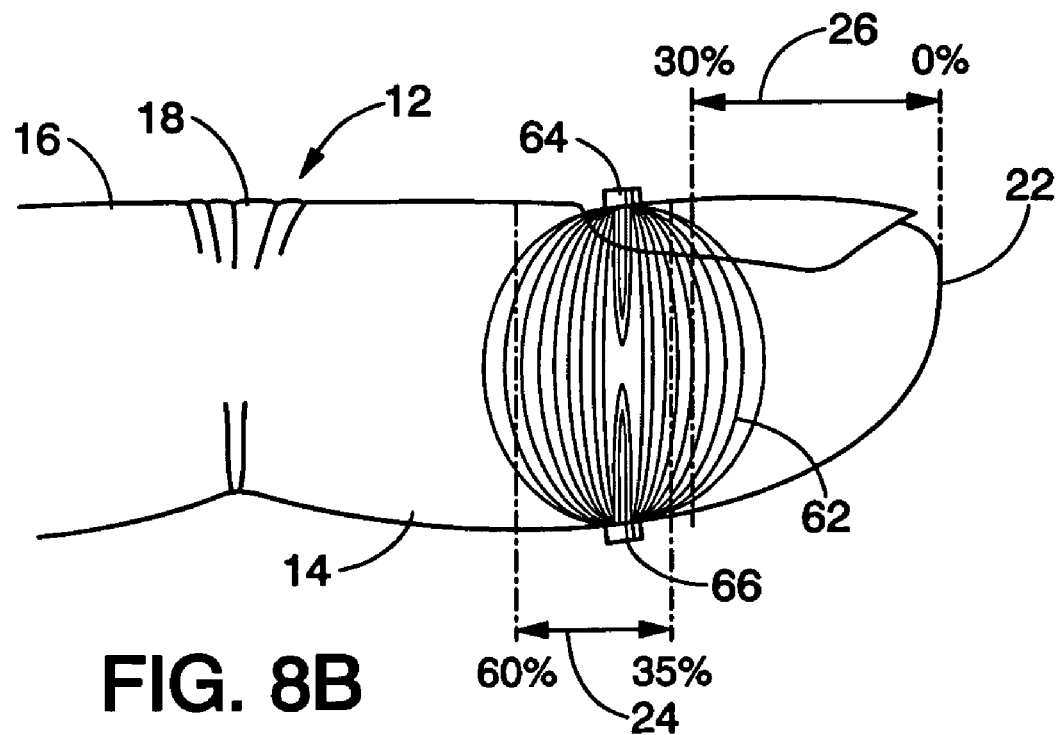
FIG. 8B illustrates an exemplary photon distribution through a patient's finger for a pulse oximetry sensor placed on a cuticle region of a patient's finger.

In contrast, FIG. 8B illustrates a photon distribution 62 created by a conventional sensor located in the cuticle region 24 of a patient's finger. The photon distribution 62 illustrates the amount of light emitted from an emitter 64 that passes through various portions of the patient's finger 12 and that is detected by a detector 66. Similar to the photon distribution 60, the photon distribution 62 is a graphical representation of where the photons from the emitter 64 travel through the tissue for ultimate receipt by the detector 66. With the emitter 64 and detector 66 located in the cuticle region 24 of the patient's finger 12, it can be seen that the majority of the photons received by the detector 66 pass through the cuticle region 24, with a minority of the photons received by the detector 66 passing through the distal region 26. Indeed, it is estimated that approximately 65% to 85% of the light received by the detector 66 has passed through the cuticle region 24 when the sensor is located in the cuticle region 24 of the patient's finger 12, whereas only approximately 15% to 35% of the light received by the detector 66 has passed through the distal region 26.

As demonstrated by the exemplary photon distributions 60 and 62 illustrated in FIGS. 8A and 8B, the placement of an emitter and detector in the distal region 26 of a patient's finger 12 results in much more of the detected light having passed through the well-perfused and relatively unoccluded tissue of the distal region 26, as opposed to the relatively occluded tissue of the cuticle region 24, when compared with the placement of an emitter and detector in the conventional cuticle region 24 of a patent's finger. As a result, the collected light presumably correlates better with the characteristics of the blood that the pulse oximeter 50 is attempting to measure, since the collected light is not as adversely affected by strongly light-absorbing or scattering structures, such as bones and larger blood vessels.

Although the present drawings illustrate the emitter 32 and the detector 34 as being wholly located in the distal region 26, it should be noted that similar results will likely follow so long as the center points of the emitter 32 and detector 34 are located in the distal region 26 even though a portion of the emitter 32 and/or detector 34 might lie in the cuticle region 24. Indeed, in a possible embodiment in which the emitter 32 and/or the detector 34 have relatively large diameters, in the range of about 5 mm to about 10 mm for example, a portion of the emitter 32 and/or detector 34 might lie in the cuticle region 24, even though the emitter 32 and the detector 34 are centered over the distal region 26. Nevertheless, it is believed that such a sensor placement would result in benefits similar to those discussed above in embodiments in which the emitter 32 and the detector 34 are wholly located in the distal region 26 without extending into the cuticle region 24.

Figure 8C:
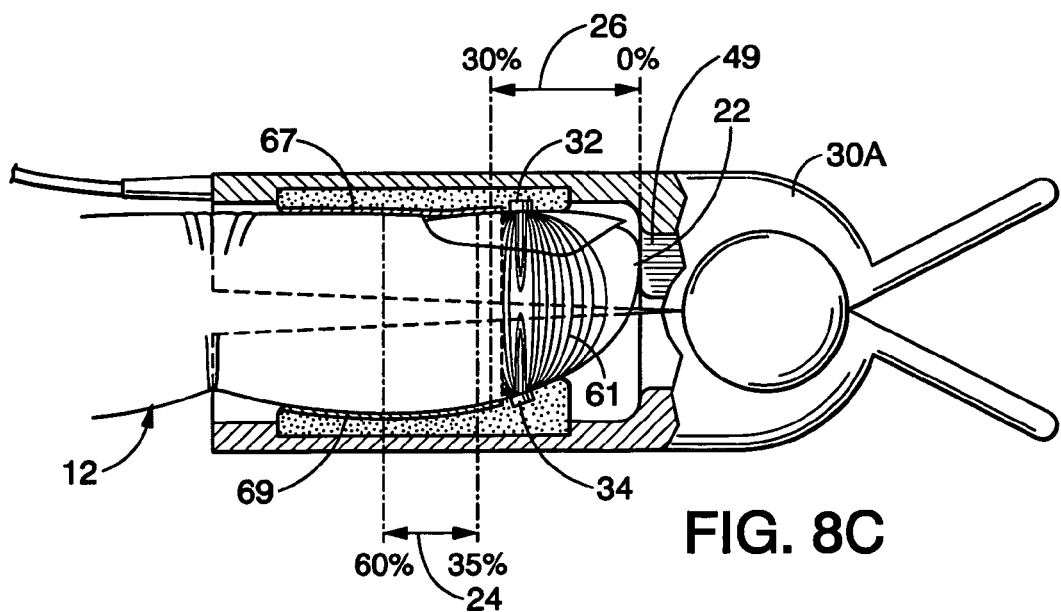
FIG. 8C illustrates a cross-sectional view of an exemplary clip-style pulse oximetry sensor having a light absorbing material and having an emitter and detector located on a distal region of a patient's finger with an exemplary photon distribution through the patient's finger.

To improve the concentration of light in the distal region 26 as opposed to the cuticle region 24, the sensor 30/30A may be provided with portions of light absorbing material in the areas of the sensor 30/30A proximate to the cuticle region 24 and portions of relatively reflective material in portions of the sensor 30/30A proximate to the distal region 26. As discussed previously, FIG. 3D illustrates a sensor 30 having portions 41 and 43 of relatively light absorbing material to facilitate such an improvement in photon distribution in the distal region 26. Further, FIG. 8C illustrates a clip-style sensor 30A that includes portions 67 and 69 of relatively light absorbing material that extends along the portions of the sensor 30A that are proximate the cuticle region 24. As illustrated by the exemplary photon distribution 61, the portions 67 and 69 of light absorbing material greatly reduce the amount of light from the emitter 32 that passes through the cuticle region 24 to be received by the detector 34. Hence, the collected light presumably correlates better with the characteristics of the blood that the pulse oximeter 50 is attempting to measure, since the collected light is not as adversely effected by structures in the cuticle region 24 of the patient's finger 12.

Figure 9:
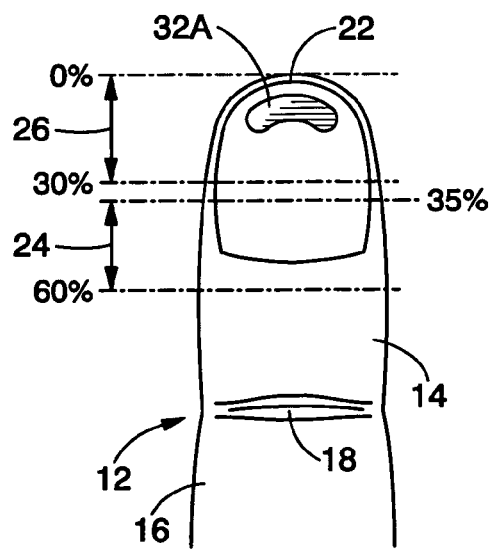
FIG. 9 illustrates a top view of an exemplary patient's finger illustrating an exemplary emitter aperture on a distal region of the patient's finger.

Alternatively, or in addition to, the above techniques, the emitter, or the aperture through which the emitter transmits light, may be shaped to enhance the concentration of photons delivered to the distal region 26. Referring to FIG. 9, an example of such an emitter/aperture 32A is illustrated. As can be seen, the emitter/aperture 32A is shaped so that it extends laterally across the distal region 26 to deliver photons having a distribution pattern that is more focused and better distributed within the distal region 26 as compared with a round emitter/aperture.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents using principles of pulse oximetry. For example, using the same, different, or additional wavelengths, the present techniques may be utilized for the measurement and/or analysis of carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A pulse oximetry sensor adapted for use on a patient's digit, wherein the patient's digit includes a distal portion having a distal bone covered with skin and tissue and wherein the distal portion has a length L as measured from a tip of the digit to a transverse fold of skin located generally at a joint between the distal bone and an adjacent bone, the pulse oximetry sensor comprising:
    an emitter and a detector adapted to be located on a distal region of the distal portion of the patient's digit when the sensor is properly applied to the patient's digit, wherein the distal region is measured as extending from the tip of the distal portion to a location spaced no more than approximately 30% of the length L from the tip, and wherein approximately 30% of the length L is in the range of approximately 5-7 mm; and
    a clip-style sensor in which the emitter and detector are disposed, wherein the clip-style sensor is configured such that the tip of the patient's digit abuts a stop within the clip-style sensor when the sensor is properly applied to the patient's digit.

2. The pulse oximetry sensor, as set forth in claim 1, wherein the emitter and the detector are adapted to operate in a transmission mode.

3. The pulse oximetry sensor, as set forth in claim 1, wherein the emitter and the detector are configured to be wholly disposed in the distal region.

4. The pulse oximetry sensor, as set forth in claim 1, wherein center points of the emitter and the detector are configured to be located in the distal region.

5. The pulse oximetry sensor, as set forth in claim 4, wherein a portion of at least one of the emitter and the detector is configured to be located on the distal portion outside the distal region.

6. The pulse oximetry sensor, as set forth in of claim 1, wherein the emitter and the detector are adapted to be located on a finger, the distal bone comprising a distal phalange of the finger.

7. The pulse oximetry sensor, as set forth in claim 1, wherein the emitter and the detector are adapted to be located on a distal segment of the distal region of the distal portion, wherein the distal segment is measured as extending from the tip of the distal portion to a location spaced no more than approximately 20% of the length L from the tip.

8. A method for performing pulse oximetry, the method comprising:
    placing an emitter and a detector of a pulse oximetry sensor on a distal region of a distal portion of a patent's digit to facilitate acquisition of a blood oxygen saturation measurement, wherein:
        the distal portion of the patient's digit includes a distal bone covered with skin and tissue;
        the distal portion has a length L as measured from a tip of the digit to a transverse fold of skin located generally at a joint between the distal bone and an adjacent bone;
        the distal region of the distal portion of the patient's digit is measured as extending from the tip of the distal portion to a location spaced no more than approximately 30% of the length L from the tip; and
        approximately 30% of the length L is in the range of approximately 5-7 mm.

9. The method, as set forth in claim 8, wherein placing comprises wrapping an adhesive bandage about the patient's digit to hold the emitter and the detector of the pulse oximetry sensor in place on the distal region.

10. The method, as set forth in claim 8, wherein placing comprises properly clipping the sensor to the patient's digit to hold the emitter and the detector in place on the distal region and wherein clipping the sensor to the patient's digit comprises advancing the patient's digit into the sensor until the patient's digit abuts a stop disposed within the sensor.

11. The method, as set forth in claim 8, comprising:
    positioning the emitter on a top portion of the distal region of the distal portion of the patient's digit;
    positioning the detector on a bottom portion of the distal region of the distal portion of the patient's digit; and
    operating the emitter and the detector in a transmission mode.

12. The method, as set forth in claim 8, comprising:
    positioning the emitter and the detector on a top portion of the distal region of the distal portion of the patient's digit; and
    operating the emitter and the detector in a reflectance mode.

13. The method, as set forth in claim 8, comprising:
    positioning the emitter and the detector on a bottom portion of the distal region of the distal portion of the patient's digit; and
    operating the emitter and the detector in a reflectance mode.

14. The method, as set forth in claim 8, comprising:
    positioning the emitter and the detector side by side in the distal region of the distal portion of the patient's digit; and
    operating the emitter and the detector in a reflectance mode.

15. The method, as set forth in claim 8, comprising placing the emitter and the detector of the pulse oximetry sensor on a distal segment of the distal region of the distal portion of the patient's digit, wherein the distal segment is measured as extending from the tip of the distal portion to a location spaced no more than approximately 20% of the length L from the tip.

16. A method of manufacturing a pulse oximetry sensor to monitor a distal region of a distal portion of a patient's digit, wherein the distal portion includes a distal bone covered with skin and tissue and wherein the distal portion has a length L as measured from a tip of the digit to a transverse fold of skin located generally at a joint between the distal bone and an adjacent bone, wherein the distal region is measured as extending from the tip of the distal portion to a location spaced no more than approximately 30% of the length L from the tip, and wherein approximately 30% of the length L is in the range of approximately 5-7 mm, the method comprising:
    providing a clip-style sensor body configured to be coupled to a distal portion of a patient's digit;
    coupling an emitter and a detector to the clip-style sensor body such that the emitter and the detector are adapted to be located on the distal region of the distal portion of the patient's digit when the clip-style sensor body is properly applied to the digit, wherein coupling the emitter and the detector to the clip-style sensor body comprises disposing the emitter on one side of the clip-style sensor body and disposing the detector on another side of the clip-style sensor body; and
    providing a stop disposed within the clip-style sensor body and configured to abut the patient's digit when the clip-style sensor body is properly applied to the patient's digit.

17. The method, as set forth in claim 16, comprising coupling the emitter and the detector to the clip-style sensor body such that the emitter and the detector are adapted to be located on a distal segment of the distal region of the distal portion of the patient's digit, wherein the distal segment is measured as extending from the tip of the distal portion to a location spaced no more than approximately 20% of the length L from the tip.

18. A pulse oximetry system comprising:
a pulse oximetry monitor; and
a clip-style pulse oximetry sensor having an emitter and a detector adapted to be located on a distal region of a distal portion of a patient's digit when the clip-style sensor is properly applied to the patient's digit, wherein:
the distal portion of the patient's digit includes a distal bone covered with skin and tissue;
the distal portion has a length L as measured from a tip of the digit to a transverse fold of skin located generally at a joint between the distal bone and an adjacent bone;
the distal region is measured as extending from the tip of the distal portion to a location spaced no more than approximately 30% of the length L from the tip;
the emitter and the detector are adapted to be located no more than approximately 5-7 mm from the tip of the patient's digit when the sensor is properly applied to the patient's digit; and
the clip-style sensor is configured such that the tip of the patient's digit abuts a stop within the clip-style sensor when the clip-style sensor is properly applied to the patient's digit.

19. The pulse oximetry system, as set forth in claim 18, wherein the emitter and the detector are adapted to operate in a transmission mode.

20. The pulse oximetry system, as set forth in claim 18, wherein the emitter and the detector are configured to be wholly disposed in the distal region.

21. The pulse oximetry system, as set forth in claim 18, wherein center points of the emitter and the detector are configured to be located in the distal region.

22. The pulse oximetry system, as set forth in claim 21, wherein a portion of at least one of the emitter and the detector is configured to be located on the distal portion outside the distal region.

23. The pulse oximetry system, as set forth in claim 18, wherein the emitter and the detector are adapted to be located on a finger, the distal bone comprising a distal phalange of the finger.

24. The pulse oximetry system, as set forth in claim 18, wherein the emitter and the detector are adapted to be located on a distal segment of the distal region of the distal portion of the patient's digit, wherein the distal segment is measured as extending from the tip of the distal portion to a location spaced no more than approximately 20% of the length L from the tip.

25. A pulse oximetry sensor adapted for use on a patient's digit, the pulse oximetry sensor comprising:

an emitter adapted to transmit light into the patient's digit; and
a detector adapted to receive the transmitted light from the patient's digit, wherein:
the detector is configured to receive at least approximately 50% of the received light from a distal region of a distal portion of the patient's digit when the pulse oximetry sensor is properly applied to the patient's digit;
the distal portion of the patient's digit includes a distal bone covered with skin and tissue; the distal portion has a length L as measured from a tip of the digit to a transverse fold of skin located generally at a joint between the distal bone and an adjacent bone;the distal region is measured as extending from the tip of the distal portion to a location spaced no more than approximately 30% of the length L from the tip; and
approximately 30% of the length L is in the range of approximately 5-7 mm: and
a clip-style sensor body in which the emitter and detector are disposed, wherein the clip-style sensor body is configured such that the tip of the patient's digit abuts a stop within the clip-style sensor body when the sensor is properly applied to the patient's digit.

26. The pulse oximetry sensor, as set forth in claim 25, wherein the emitter and the detector are adapted to operate in a transmission mode.

27. The pulse oximetry sensor, as set forth in claim 25, wherein the emitter and the detector are adapted to be wholly disposed in the distal region.

28. The pulse oximetry sensor, as set forth in claim 25, wherein the emitter and the detector have center points that are adapted to be located in the distal region.

29. The pulse oximetry sensor, as set forth in claim 28, wherein a portion of at least one of the emitter and the detector is adapted to be located on the distal portion outside the distal region.

30. The pulse oximetry sensor, as set forth in claim 25, wherein the emitter is configured to emit light into a finger and the detector is adapted to receive the transmitted light from the finger, the distal bone comprising a distal phalange of the finger.

31. The pulse oximetry sensor, as set forth in claim 25, wherein the detector is positioned to receive at least approximately 50% of the received light from a distal segment of the distal region of the distal portion of the patient's digit, wherein the distal segment is measured as extending from the tip of the distal portion to a location spaced no more than approximately 20% of the length L from the tip.

32. The pulse oximetry sensor, as set forth in claim 25, wherein the detector is adapted to receive approximately 50% to 80% of the received light from the distal region of the distal portion of the patient's digit.

* * * * *